United States Patent [19]

Pozzi et al.

[11] Patent Number: 4,912,138
[45] Date of Patent: Mar. 27, 1990

[54] PHARMACEUTICAL PREPARATION CONTAINING THIAMPHENICOL FOR VETERINARY USE

[75] Inventors: Franco Pozzi, Como; Claudia Tortora, Paderno Dugnano; Angelo Carenzi, Busto Arsizio, all of Italy

[73] Assignee: Zambon S.p.A., Milan, Italy

[21] Appl. No.: 95,673

[22] Filed: Sep. 14, 1987

[30] Foreign Application Priority Data

Sep. 15, 1986 [IT] Italy .................... 21695 A/86

[51] Int. Cl.$^4$ .................... A61K 31/03; A61K 31/395
[52] U.S. Cl. .................... 514/628; 514/424; 514/408; 514/665; 514/666; 514/646
[58] Field of Search ............ 514/628, 359, 408, 424, 514/646, 663, 665, 666

[56] References Cited

U.S. PATENT DOCUMENTS

| | | | |
|---|---|---|---|
| 3,957,994 | 5/1976 | Schroer | 424/253 |
| 4,188,402 | 2/1980 | Portelli | 514/628 X |
| 4,235,892 | 11/1980 | Nagabhushan | 514/626 X |
| 4,291,013 | 9/1981 | Wahlig | 514/773 |
| 4,361,557 | 11/1982 | Nagabhushan | 514/551 X |
| 4,575,506 | 3/1986 | Della Bella | 514/282 |
| 4,705,803 | 11/1987 | Kern | 514/450 |

FOREIGN PATENT DOCUMENTS

| | | |
|---|---|---|
| 0022342 | 1/1981 | European Pat. Off. . |
| 3440140 | 10/1976 | Fed. Rep. of Germany . |
| 2615140 | 6/1985 | Fed. Rep. of Germany . |
| 38-25692 | 12/1963 | Japan . |
| 1538903 | 1/1979 | United Kingdom . |
| 2000970 | 1/1979 | United Kingdom . |

Primary Examiner—William R. Dixon, Jr.
Assistant Examiner—James M. Hunter, Jr.
Attorney, Agent, or Firm—Stevens, Davis, Miller & Mosher

[57] ABSTRACT

Pharmaceutical preparations for veterinary use, in the form of concentrate solutions, containing Thiamphenicol as active ingredient are described. Such pharmaceutical preparations with antibiotic activity have the following compositions:

| | |
|---|---|
| TAF | 10–25% |
| Polyethylene glycol with average molecular weight between 200 and 400 | 45–62% |
| Pharmaceutically acceptable aprotic polar solvent selected between N—methyl-2-pyrrolidone and 2-pyrrolidone | 23–29% |
| the whole being 100% | |

13 Claims, No Drawings

PHARMACEUTICAL PREPARATION CONTAINING THIAMPHENICOL FOR VETERINARY USE

SUMMARY OF THE INVENTION

The present invention concerns a pharmaceutical preparation for veterinary use with antibiotic activity and more particularly it concerns a pharmaceutical preparation for veterinary use containing Thiamphenicol as active ingredient.

Thiamphenicol [D-threo-2-dichloroacetamido-1-(4-methylsulfonyl)-1,3-propanediol] (Merck Index, 10th edition, No. 9140) is a known antimicrobial drug.

It is used in veterinary therapy on many breeding animal species. Its broad activity spectrum makes it particularly useful in the treatment of many infections diseases and, especially, of bacterial infections in respiratory tract.

The use of pharmaceutical preparations in veterinary therapy meets with particular features and problems which are due mostly to the diffusion of the usual breeding-techniques which make easier a fast spreading of infections.

Then, in case of contagious diseases, the presence of just few diseased animals requests a rapid and global intervention on all the animals of the breeding to avoid the infection.

For this purpose the administration of drugs is carried out with medicated feed or through drinking-water.

The use of medicated feed is certainly more unfavourable from both the practical and the economic point of view.

Besides the disadvantage in needing a relatively long period of time for its preparation, the therapy with medicated feed presents difficulties in the dosage too.

In fact, there is often the risk of sub-dosage just in diseased animals which usually eat less.

On the contrary, the animals, even if they are sick, feel by instinct the need of drinking.

Therefore, for the above indicated reasons, the administration to the animals of active ingredients in the form of water-soluble pharmaceutical preparations, when possible, is always preferable. In fact, the therapeutica treatment through drinking-water shows remarkable advantages such as the rapidity and the immediacy of intervention, the high degree of therapeutic effectiveness, the modulation of the period of treatment and the better settlement of the dosage of active ingredient used.

Moreover, a water-soluble pharmaceutical preparation is equally suitable for being administered in milk, for example in case of treatment of calves.

DETAILED DESCRIPTION OF THE INVENTION

Thiamphenicol (hereinafter indicated as TAF) is a powder with a low water-solubility and with a very slow dissolution kinetics. Then, its eventual dissolution in distribution reservoirs of drinking-water would need a very long period of time and heating. Besides, because of the low solubility of TAF, there is the risk of obstructing the distribution devices, if the product reprecipitates.

TAF has a low solubility also in many pharmaceutically acceptable organic solvents such as 1,2-propanediol, 1,3-butanediol, glycerin as well as in the most common excipients for liquid preparations such as polysorbate and polyethyleneglycol.

On the contrary TAF is generally soluble in aprotic polar solvents but most of them are not suitable in pharmaceutical preparation for their toxicity.

In addition to that if a solution of TAF in a pharmaceutically acceptable aprotic polar solvent, such as 2-pyrrolidone or N-methyl-2-pyrrolidone, is added with water, TAF reprecipitates at once.

We have now surprisingly found, and this is the object of the present invention, a pharmaceutical preparation containing TAF which has a complete and fast solubility in water and which can be stored in usual storage-conditions without leading to chemical degradation or forming precipitates.

Such pharmaceutical preparation is a concentrated solution of TAF which may be diluted in water or milk at the moment of use.

The pharmaceutical preparation according to the present invention consists of (percentage in weight):

| | |
|---|---|
| TAF | 10-25% |
| Polyethylene glycol with average molecular weight between 200 and 400 | 45-62% |
| Pharmaceutically acceptable aprotic polar solvent selected between N-methyl-2-pyrrolidone and 2-pyrrolidone | 23-29% |
| the whole being 100% | |

Suitable Polyethylene glycols are PEG 200, 300 and 400 (the number following the abbreviation indicates the average molecular weight of polyethylene glycol).

The pharmaceutical preparations in the form of concentrated solutions according to the present invention, have a complete and immediate solubility in water.

They allow the preparation of diluted solutions of TAF which are stable in the time also at low temperatures.

So, the therapeutic intervention can be immediate and settled in the period and in the dosage in relation to the conditions and to the animal species.

The pharmaceutical preparations object of the present invention are particularly useful in the therapy of infections due to TAF-sensitive micro-organisms in calves, swine and poultry.

Specific examples of preparations according to the present invention are the following (percentage in weight)

| | | |
|---|---|---|
| (a) | TAF | 20.0% |
| | PEG 200 | 55.0% |
| | 2-pyrrolidone | 25.0% |
| (b) | TAF | 12.5% |
| | PEG 300 | 60.0% |
| | N-methyl-2-pyrrolidone | 27.5% |
| (c) | TAF | 20.0% |
| | PEG 200 | 55.0% |
| | N-methyl-2-pyrrolidone | 25.0% |
| (d) | TAF | 10.0% |
| | PEG 400 | 61.9% |
| | N-methyl-2-pyrrolidone | 28.1% |
| (e) | TAF | 12.5% |
| | PEG 300 | 60.0% |
| | 2-pyrrolidone | 27.5% |
| (f) | TAF | 25.0% |
| | PEG 300 | 46.0% |
| | 2-pyrrolidone | 29.0% |
| (g) | TAF | 12.5% |
| | PEG 200 | 60.0% |
| | 2-pyrrolidone | 27.5% |
| (h) | TAF | 12.5% |

-continued

|   |                     |        |
|---|---------------------|--------|
|   | PEG 200             | 60.0%  |
|   | N-methyl-2-pyrrolidone | 27.5% |
| (i) | TAF               | 20.0%  |
|   | PEG 300             | 55.0%  |
|   | 2-pyrrolidone       | 25.0%  |
| (l) | TAF               | 20.0%  |
|   | PEG 300             | 55.0%  |
|   | N-methyl-2-pyrrolidone | 25.0% |

The compositions object of the present invention are prepared according to simple usual techniques and distributed in bottles in the desired weight.

The package allows to dilute easily the concentrated solution of TAF into the tanks of drinking-water up to the desired concentration which concentration will depend on the kind of animal and on the pathologic disease present in the breeding.

In order to better illustrate the present invention, the following examples are now given.

EXAMPLE 1

A solution consisting of:

| TAF                    | 10.0 kg |
|------------------------|---------|
| N-methyl-2-pyrrolidone | 12.5 kg |
| PEG 200                | 27.5 kg | is prepared by working according to the following procedure: N-methyl-2-pyrrolidone is heated at 50° C. and TAF is dissolved in it. Then, PEG 200 is added and the whole is left to cool at room temperature, filtered and distributed into 50 polyethylene bottles.

EXAMPLE 2

A solution consisting of:

| TAF           | 10.0 kg |
|---------------|---------|
| 2-pyrrolidone | 12.5 kg |
| PEG 200       | 27.5 kg | is prepared according to the procedure described in example 1 and distributed into 50 polyethylene bottles.

EXAMPLE 3

A solution consisting of:

| TAF                    | 6.25 kg  |
|------------------------|----------|
| N-methyl-2-pyrrolidone | 13.75 kg |
| PEG 200                | 30.00 kg | is prepared according to the procedure described in example 1 and distributed into 50 polyethylene bottles.

EXAMPLE 4

A solution consisting of:

| TAF           | 6.25 kg  |
|---------------|----------|
| 2-pyrrolidone | 13.75 kg |
| PEG 300       | 30.00 kg | is prepared according to the procedure described in example 1 and distributed into 50 polyethylene bottles.

By working in a similar, the other compositions reported at pages 4 and 5 are prepared.

EXAMPLE 5

The compositions described in the above examples were stored for a year in environmental storage conditions and for 6 months they were exposed to thermic shock (10°–30° C.). The examination of the solution and the chemical analysis of the active ingredient did not show any precipitation or any degradation of TAF.

Even after 3 years in environmental storage conditions no precipitation could be evidentiated.

The chemical analysis of TAF showed a degree of degradation lower than 3%.

What we claim is:

1. Pharmaceutical preparation for veterinary use consisting of:

| TAF                                            | 10–25% by weight |
|------------------------------------------------|------------------|
| Polyethylene glycol with average molecular weight between 200 and 400 | 46–62% by weight |
| Pharmaceutically acceptable aprotic polar solvent selected from the group consisting of N—methyl-2-pyrrolidone and 2-pyrrolidone | 23–29% by weight |
| the whole being 100%.                          |                  |

2. Pharmaceutical preparation according to claim 1 in which polyethylene glycol is selected from the group consisting of PEG 200, PEG 300 and PEG 400.

3. Pharmaceutical preparation according to claim 1 consisting of:

| TAF           | 12.5% |
|---------------|-------|
| PEG 200       | 60.0% |
| 2-pyrrolidone | 27.5%. |

4. Pharmaceutical preparation according to claim 1 consisting of:

| TAF                    | 20.0% |
|------------------------|-------|
| PEG 200                | 55.0% |
| N—methyl-2-pyrrolidone | 25.0%. |

5. Pharmaceutical preparation according to claim 1 consisting of:

| TAF           | 12.5% |
|---------------|-------|
| PEG 300       | 60.0% |
| 2-pyrrolidone | 27.5%. |

6. Pharmaceutical preparation according to claim 1 consisting of:

| TAF           | 20.0% |
|---------------|-------|
| PEG 300       | 55.0% |
| 2-pyrrolidone | 25.0%. |

7. Pharmaceutical preparation according to claim 1 consisting of:

| TAF           | 20.0% |
|---------------|-------|
| PEG 200       | 55.0% |
| 2-pyrrolidone | 25.0%. |

8. Pharmaceutical preparation according to claim 1 consisting of:

| TAF | 12.5% |
|---|---|
| PEG 300 | 60.0% |
| N—methyl-2-pyrrolidone | 27.5%. |

9. Pharmaceutical preparation according to claim 1 consisting of:

| TAF | 10.0% |
|---|---|
| PEG 400 | 61.9% |
| N—methyl-2-pyrrolidone | 28.1%. |

10. Pharmaceutical preparation according to claim 1 consisting of:

| TAF | 25.0% |
|---|---|
| PEG 300 | 46.0% |
| 2-pyrrolidone | 29.0%. |

11. Pharmaceutical preparation according to claim 1 consisting of:

| TAF | 12.5% |
|---|---|
| PEG 200 | 60.0% |
| N—methyl-2-pyrrolidone | 27.5%. |

12. Pharmaceutical preparation according to claim 1 consisting of:

| TAF | 20.0% |
|---|---|
| PEG 300 | 55.0% |
| N—methyl-2-pyrrolidone | 25.0%. |

13. Method for the treatment of infections due to TAF-sensitive micro-organisms in breeding animals consisting of administering a therapeutically effective amount of TAF by dilution in drinking-water of a preparation consisting of:

| TAF | 10–25% by weight |
|---|---|
| Polyethyleneglycol with average molecular weight between 200 and 400 | 46–62% by weight |
| Pharmaceutically acceptable aprotic polar solvent selected from the group consisting of N—methyl-pyrrolidone and 2-pyrrolidone, the whole being 100% | 23–29% by weight. |

* * * * *